US00PP33075P2

(12) United States Plant Patent
Van Swieten

(10) Patent No.: US PP33,075 P2
(45) Date of Patent: May 18, 2021

(54) ***PHALAENOPSIS* ORCHID PLANT NAMED 'PHALHINDEK'**

(50) Latin Name: ***Phalaenopsis* hybrid**
Varietal Denomination: PHALHINDEK

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/031,094

(22) Filed: Sep. 24, 2020

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHALHINDEK', particularly characterized by white, small flowers with small, very light purple centers and reddish-yellow and white lips, concave flower shape in lateral view, compact plant, and is propagated by meristem tissue culture, is disclosed.

3 Drawing Sheets

Genus and species: *Phalaenopsis* hybrid.
Variety denomination: 'PHALHINDEK'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALHINDEK'.

The new *Phalaenopsis* plant is a product of a planned breeding program conducted by the inventor in Bleiswijk, the Netherlands. The objective of this breeding program was to create a new *Phalaenopsis* plant with many attractive, white, small flowers with very light purple centers and reddish-yellow and white lips, suitable for potted plant production.

The new *Phalaenopsis* plant 'PHALHINDEK' is a result of cross-pollination made by the inventor in December 2010 in Bleiswijk, the Netherlands, of the proprietary female, or seed parent, *Phalaenopsis* hybrid '23979-09' (unpatented) with the proprietary male, or pollen parent, *Phalaenopsis* hybrid '11469-0002' (unpatented).

The new *Phalaenopsis* was selected by the inventor as a single plant within the progeny of the stated cross-pollination in a controlled greenhouse in Bleiswijk, the Netherlands, in November 2013. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 16, 2019 (Application no. 2019/0992), by Applicant who obtained the subject matter disclosed directly from the inventor. 'PHALHINDEK' has not been made publicly available or sold anywhere in the world prior to the effective filing date of this application with the exception of sales or disclosures made one year or less before the effective filing date of this claimed invention by Applicant who obtained 'PHALHINDEK' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALHINDEK' as a new and distinct variety of *Phalaenopsis* plant:

1) White, small flowers with small, very light purple centers and reddish-yellow and white lips;
2) Flower shape in lateral view is concave; and
3) Plant is compact.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, the Netherlands, from 42-week-old plants in August 2020. Colors in the photographs may differ from the color values cited in the detailed botanical description, which accurately describe the actual colors of the new variety.

DESCRIPTION OF THE NEW VARIETY

Figure 1:
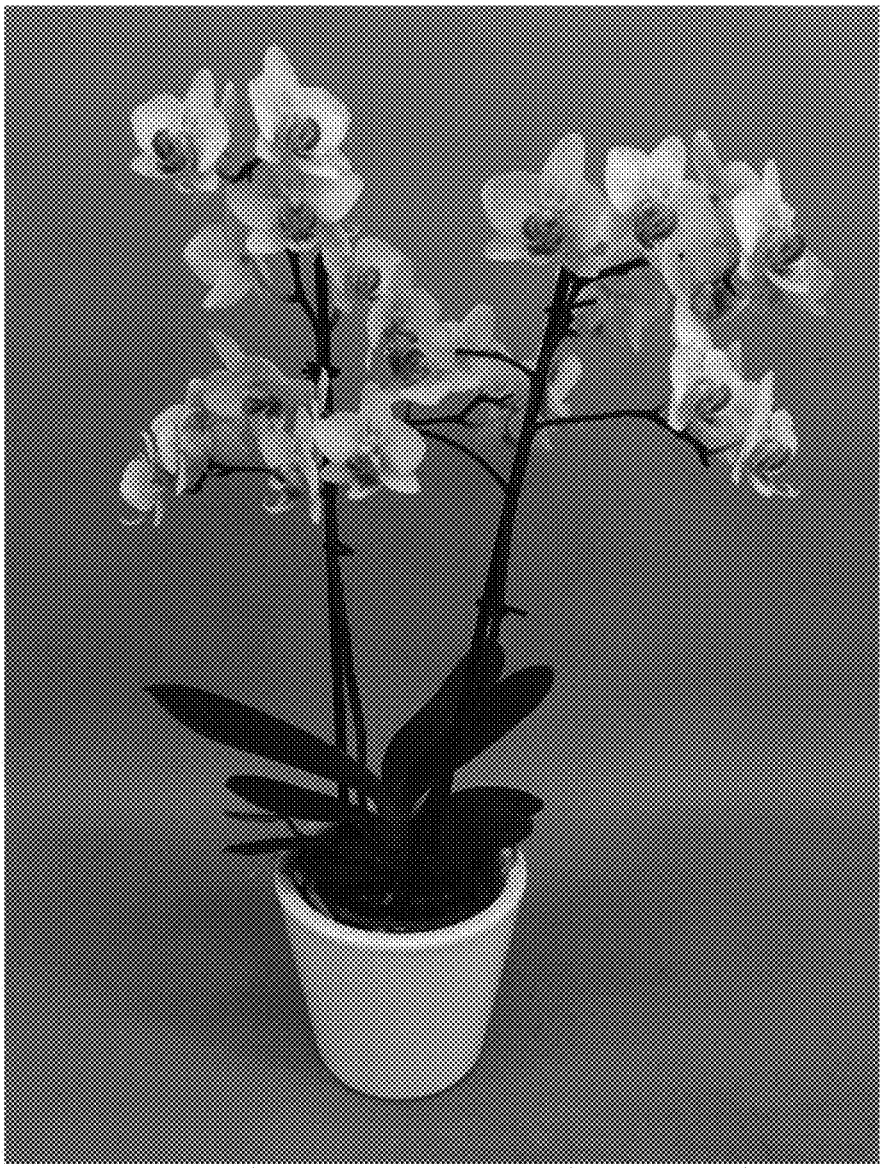
FIG. 1 shows the overall plant habit, including blooms and foliage of 'PHALHINDEK'.
Figure 2:
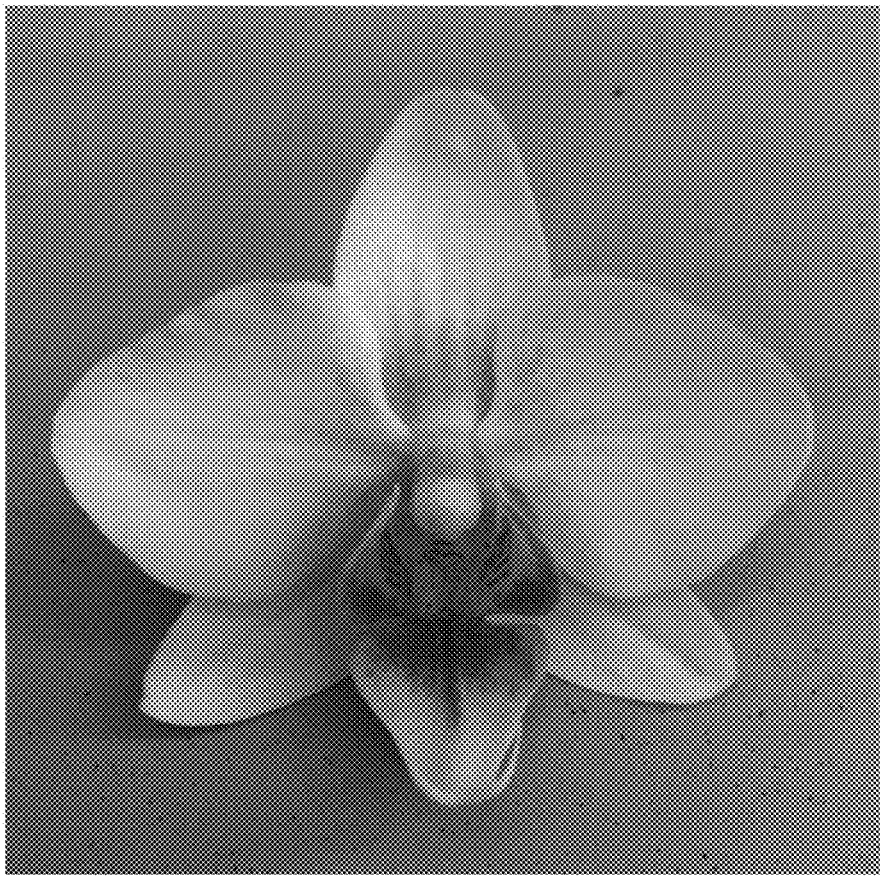
FIG. 2 shows a close-up of a flower of 'PHALHINDEK'.
Figure 3:
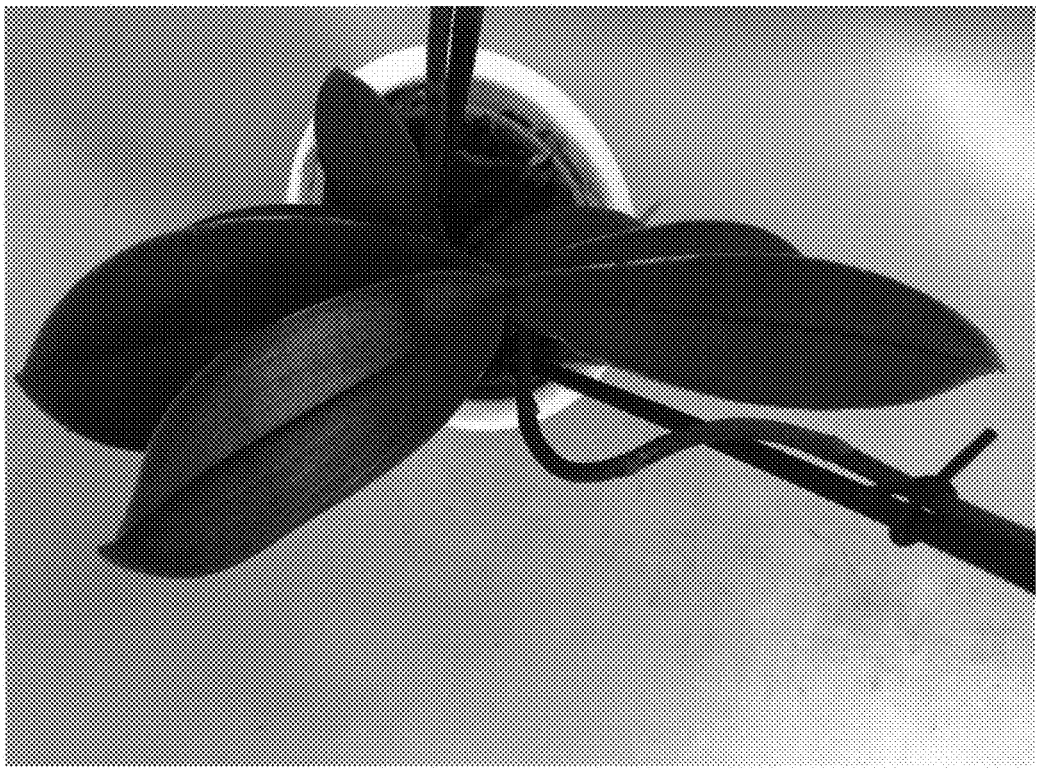
FIG. 3 shows an overhead view of the leaves of 'PHALHINDEK'.

The following detailed description sets forth the distinctive characteristics of 'PHALHINDEK'. Plants of the new

*Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in August 2020 on flowering plants which were planted in 9-centimeter (diameter) pots. After in vitro propagation, the plants were grown in nursery trays for 18-20 weeks, followed by transplantation to 9-centimeter pots and grown in a greenhouse between 27° C. to 29° C. for 25 weeks, continued by a cooling period of 6 weeks between 18° C. to 20° C. and 11 weeks in a greenhouse of 21° C. Flowering occurs after 42 weeks in 9-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALHINDEK'.

Parentage:

*Female parent*.—*Phalaenopsis* cultivar '23979-09' (unpatented).

*Male parent*.—*Phalaenopsis* cultivar '11469-0002' (unpatented).

Propagation:

*Type*.—Meristem tissue culture.

Roots:

*Root description*.—Greyed-green (something between RHS 190B and 190C) colored roots with branching lateral roots having yellow-green (RHS 144C) colored root tips.

Plant:

*Commercial crop time to flowering*.—Following asexual propagation (in vitro), the rooted cuttings grow for 18-20 weeks. After transplantation into 9-cm pots, the plants are finished after 40 to 42 weeks.

*Growth habit of the peduncle*.—Upright to slightly pendent with panicle inflorescence.

*Height* (*from soil level to top of inflorescence*).—Approximately 30.0 cm to 35.0 cm.

*Width* (*measured from leaf tips*).—About 21.0 cm to 23.0 cm.

*Vigor*.—Strong.

Leaves:

*Mature leaves*.—Quantity per plant: 8 to 10 leaves are produced before flowering. Length (fully expanded): 10.0 cm to 13.0 cm. Width: 4.0 cm to 5.0 cm. Position of the broadest part of the leaf: At the middle. Shape: Narrow oblong. Base shape: Moderately elongated. Apex: Obtuse unequal. Leaf blade angle with the petiole (measured from the horizontal position): Between 20 degrees and 35 degrees. Leaf margin: Entire. Color: Upper surface: RHS 147A. Lower surface: RHS 146A. Texture (both upper and lower surfaces): Smooth. Thickness: 2.5 mm to 2.9 mm. Variegation: Absent. Venation: Pattern: Parallel. Color of the midvein: Upper surface: RHS 147A. Lower surface: RHS 146A.

Peduncle:

*Quantity per plant*.—1 to 2.

*Number of flowers per peduncle*.—14 to 20.

*Length*.—30.0 cm to 35.0 cm.

*Diameter*.—3.8 mm to 4.3 mm.

*Strength*.—Strong.

*Aspect*.—Upright to slightly pendent.

*Texture*.—Smooth.

*Color*.—Green (RHS 146B) with a touch of reddish-brown (RHS 200B).

*Internode length*.—2.0 cm to 3.0 cm.

Inflorescence description:

*Appearance*.—Upright to slightly pendent, panicle inflorescence with bilaterally symmetrical flowers that open in succession beginning with the lowermost flower.

*Number of inflorescences*.—1 to 2.

*Inflorescence size*.—Height (from base to tip): 150.0 mm to 170.0 mm.

*Flowering time*.—First flowers can be expected 7 to 8 months after planting in a 9-cm pot.

*Flower*.—Height: 40.0 mm to 45.0 mm. Diameter: 50.0 mm to 55.0 mm. Depth of lip: 18.0 mm to 20.0 mm.

*Flower longevity*.—On the plant: 12 to 14 weeks.

*Flower shape*.—Concave.

*Fragrance*.—Absent.

*Flower bud*.—Average size: Medium. Length: 18.0 mm to 20.0 mm. Width: 16.0 mm to 18.0 mm. Shape: Egg shaped. Color: Yellow-green (something in between RHS 154D and 145C) with a touch of RHS 182B.

*Petals*.—Arrangement: Open/free. Shape: Semi-circular. Apex: Obtuse asymmetric. Margin: Weakly undulated. Length (from base to tip): 23.0 mm to 25.0 mm. Width: 22.0 mm to 24.0 mm. Position of the broadest part of the petal: Toward the base. Color (when fully opened): Upper surface: Basic color: White (RHS NN155C). Over color: Shaded (RHS 76B) at the base. Lower surface: Basic color: White (RHS NN155C). Over color: Shaded (RHS 76A) at the base. Number of spots and stripes on the petals (upper surface): None. Color of spots and stripes on the petals (upper surface): Not applicable. Density of netting of the petals (upper surface): None. Color of the netting (upper surface): Not applicable.

*Dorsal sepal*.—Shape: Elliptic. Apex: Emarginated symmetric. Margin: Entire. Length (from base to tip): 24.0 mm to 26.0 mm. Width: 14.0 mm to 16.0 mm. Position of the broadest part of the dorsal sepals: At the middle. Color (when fully opened): Upper surface: Basic color: White (RHS NN155C). Over color: Shaded (RHS 76A) at the base. Lower surface: Basic color: White (RHS NN155C). Over color: Shaded (RHS N78D). Number of spots and stripes on the dorsal sepals (upper surface): None. Color of spots and stripes on the dorsal sepals (upper surface): Not applicable. Density of netting of the dorsal sepals (upper surface): None. Color of the netting: Not applicable.

*Lateral sepals*.—Shape: Ovate. Apex: Obtuse asymmetric. Margin: Entire. Length (from base to tip): 25.0 mm to 27.0 mm. Width: 13.0 mm to 15.0 mm. Position of the broadest part of the lateral sepals:

Toward the base. Color (when fully opened): Upper surface: Basic color: White (RHS NN155C). Over color: Touch of yellow-green (RHS 145D) at the base and very light purple (RHS 76B) at the base. Lower surface: Basic color: White (RHS NN155C). Over color: Touch of light yellow-green (RHS 145D) and very light purple (RHS 76B) at the base; very light purple midvein (RHS 76B). Number of spots, dots, and stripes on the lateral sepals (upper surface): Few to medium very small dots at the base. Color of spots, dots, and stripes on the lateral sepals (upper surface): RHS N77B. Density of netting of the lateral sepals (upper surface): None. Color of the netting (upper surface): Not applicable.

*Labellum* (*lip*).—Whiskers: Present. Length of whiskers: 5.0 mm to 7.0 mm. Color of whiskers: White (RHS NN155C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Undulated (widely wavy). Length: 7.0 mm to 9.0 mm. Width: 6.0 mm to 8.0 mm. Color: Upper surface: Yellow (RHS 13A) at the base and (RHS 4D) with red stripes (RHS 184A); white (RHS 155D) at the middle; purplish-pink (RHS N78C) toward the top. Lower surface: White (RHS 155D) at the base; reddish (RHS 184B) on one side; light reddish-purple (RHS N78D) toward the tip. Number of spots and stripes on the lateral lobe: Few stripes at the base. Color of spots and stripes on the lateral lobe: RHS 184A. Density of netting of the lateral lobe: None. Color of the netting: Not applicable.

*Apical lobe*.—Shape: Triangular. Margin: Entire. Length: 18.0 mm to 20.0 mm. Width: 9.0 mm to 11.0 mm. Color: Upper surface: Yellow (RHS 13A) and red (RHS 184B) at the base; white (RHS NN155C) toward whiskers. Lower surface: Yellow (something in between RHS 13C and 13D) toward wings with small red dots (RHS 184B); white (RHS NN155C) toward whiskers. Number of spots, dots, and stripes on the apical lobe: Few to medium very small dots. Color of spots, dots, and stripes on the apical lobe: RHS 184B. Density of netting of the apical lobe: None. Color of the netting: None.

*Callus*.—Average size: Medium. Height: 5.0 mm to 6.0 mm. Length: 5.0 mm to 6.0 mm. Width: 4.0 mm to 5.0 mm. Color: Orange-yellow (RHS 21A); dotted (RHS 176A).

Reproductive organs:

*Column*.—Length: 6.0 mm to 8.0 mm. Diameter: 4.0 mm to 4.3 mm. Color: Light reddish-purple (RHS N78D) with white tip (RHS NN155C).

*Pollinia*.—Quantity: 2. Diameter: 0.5 mm to 0.7 mm. Color: Orange (RHS 24A).

*Ovary*.—Length: 10.0 mm to 12.0 mm. Diameter: 1.6 mm to 1.8 mm.

*Pedicel*.—Length: 32.0 mm to 34.0 mm. Diameter: 1.9 mm to 2.1 mm. Texture: Smooth. Color: Hint of dark purple (something in between RHS N77A and N77B) at the base; light yellow-green (RHS 145D) and light reddish-purple (RHS N78D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALHINDEK' differs from female parent plant '23979-09' (unpatented) in that 'PHALHINDEK' has white whiskers and light reddish-purple columns with white tips, whereas '23979-09' has white whiskers with light greenish-yellow tips and white columns with few light purple dots at the base. Additionally, 'PHALHINDEK' has smaller flowers and shorter whiskers than '23979-09'.

'PHALHINDEK' differs from male parent plant '11469-0002' (unpatented) in that 'PHALHINDEK' has white whiskers and light reddish-purple columns with white tips, whereas '11469-0002' has purplish-pink whiskers with white margins and reddish-purple columns. Additionally, 'PHALHINDEK' has longer whiskers than '11469-0002'.

'PHALHINDEK' is most similar to the commercial *Phalaenopsis* plants named 'PHALDILEP' (U.S. Plant Pat. No. 29,641) and 'PHALGNAAQ' (unpatented). 'PHALHINDEK' differs from the commercial variety 'PHALDILEP' in that 'PHALHINDEK' has obtuse petal apexes and light reddish-purple columns with white tips, whereas 'PHALDILEP' has rounded petal apexes and white columns. Additionally, 'PHALHINDEK' has smaller flowers and shorter whiskers than 'PHALDILEP'.

'PHALHINDEK' differs from the commercial variety 'PHALGNAAQ' in that 'PHALHINDEK' has light reddish-purple columns with white tips and white whiskers, whereas 'PHALGNAAQ' has very light purple columns and white whiskers with yellow tips.

I claim:

1. A new and distinct variety of *Phalaenopsis* plant named 'PHALHINDEK', substantially as described and illustrated herein.

* * * * *